(12) United States Patent
Fernandez San Pablo (10) Patent No.: US 9,724,175 B2
(45) Date of Patent: Aug. 8, 2017

(54) SELF-UPRIGHTING ORTHODONTIC BRACKET ASSEMBLY AND A METHOD OF USING THE BRACKET ASSEMBLY

(71) Applicant: Rafael Fernandez San Pablo, Murcia (ES)

(72) Inventor: Rafael Fernandez San Pablo, Murcia (ES)

( * ) Notice: Subject to any disclaimer, the term of this patent is extended or adjusted under 35 U.S.C. 154(b) by 437 days.

(21) Appl. No.: 14/294,454

(22) Filed: Jun. 3, 2014

(65) Prior Publication Data
US 2015/0342707 A1    Dec. 3, 2015

(51) Int. Cl.
*A61C 7/12*     (2006.01)
*A61C 7/28*     (2006.01)
*A61C 7/14*     (2006.01)

(52) U.S. Cl.
CPC .............. *A61C 7/287* (2013.01); *A61C 7/14* (2013.01); *A61C 7/141* (2013.01); *Y10T 29/4957* (2015.01)

(58) Field of Classification Search
CPC ............. A61C 7/12; A61C 7/14; A61C 7/287
See application file for complete search history.

(56) References Cited

U.S. PATENT DOCUMENTS

| | | | | |
|---|---|---|---|---|
| 3,721,005 A | * | 3/1973 | Cohen | A61C 7/14 433/16 |
| 4,597,739 A | * | 7/1986 | Rosenberg | A61C 7/14 433/16 |
| 4,859,179 A | | 8/1989 | Kesling | |
| 4,867,678 A | * | 9/1989 | Parker | A61C 7/12 433/8 |
| 7,306,458 B1 | * | 12/2007 | Lu | A61C 7/14 433/16 |
| 8,038,438 B2 | * | 10/2011 | Ruiz Diaz | A61C 7/14 433/11 |
| 9,339,353 B2 | * | 5/2016 | Voudouris | A61C 7/287 |
| 9,408,676 B2 | * | 8/2016 | Rahimi | A61C 7/14 |
| 2013/0078595 A1 | * | 3/2013 | Solano Reina | A61C 7/141 433/10 |
| 2014/0205962 A1 | * | 7/2014 | Damon | A61C 7/22 433/13 |
| 2014/0272751 A1 | * | 9/2014 | Cosse | A61C 7/02 433/9 |

OTHER PUBLICATIONS

Peter C. Kesling, DDS, "Dynamics of the Tip-edge bracket" American Journal of Orthodoctics and Dentofacial Orthopedics., Jul. 1989; vol. 96; pp. 16-25.
Peter C. Kesling, DDS et al., "Treatment with Tip-Edge brackets and differential tooth movement" American Journal of Orthodoctics and Dentofacial Orthopedics., May 1991; vol. 99; No. 5, pp. 387-401.

* cited by examiner

*Primary Examiner* — Ralph Lewis
(74) *Attorney, Agent, or Firm* — Jacobson Holman, PLLC.

(57) ABSTRACT

The present invention represents a qualitative technique modification of the self-uprighting bracket technique. The present invention overcome the drawbacks of the prior art by providing an orthodontic bracket assembly having a base with rotatable body engaging the archwire and removable plate inserted into the base to retain the archwire. In addition, the removable plate can allow or prevent the rotation of the rotatable body depending on the different stages of the treatment.

19 Claims, 12 Drawing Sheets

SELF-UPRIGHTING ORTHODONTIC BRACKET ASSEMBLY AND A METHOD OF USING THE BRACKET ASSEMBLY

FIELD OF THE INVENTION

This invention relates to a new and improved orthodontic bracket assembly for use in edgewise wire techniques to facilitate tipping movement of a tooth and sliding of the bracket assembly along an archwire, including structure to minimize frictional resistance, thereby reducing the time of completing the movement to the desired location along the arch, and enhancing the health and comfort of the patient.

DESCRIPTION OF RELATED ART

As known in the dental art, in order to identify specific locations on a tooth, the tooth is divided into different surfaces and each surface has a specific name. The surfaces are named according to the direction in which they face. The surfaces of teeth are as follows. A "lingual" surface refers to the surface of a tooth facing the tongue. A "facial" surface refers to the surface of a tooth facing the cheeks or lips. This surface ("facial") can also be known as a "labial" surface, the surface of an anterior tooth facing the lips, and a "buccal" surface, the surface of a posterior tooth facing the cheeks. A "proximal" surface refers to the surface of a tooth that faces a neighboring tooth's surface; each tooth has two proximal surfaces. A "mesial" surface refers to the surface of a tooth that is closest to the midline (middle) of the face. A "distal" surface refers to the surface of a tooth that faces away from the midline of the face. An "occlusal" surface refers to the chewing surface of posterior teeth. An "incisal ridge (or edge)" refers to the biting edge of anterior teeth.

Orthodontic brackets are secured to a patient's teeth for use to selectively straighten the patient's teeth. One type of orthodontic bracket known in the art includes a base having a slot formed thereon. The slot is configured to receive an archwire that extends between different teeth. A stopping means is removably attached to the base for use in securing the archwire to the base. Examples of these brackets are described in Peter C. Kesling, Dynamics of the Tip-edge Bracket, Am. J. Orthod Dentofac Orthop, 1989, 96:16-25, and Peter C. Kesling et al., treatment with Tip-Edge Brackets and Differential Tooth Treatment, Am. J. Orthod Dentofac Orthop, 1991, Vol. 99, No. 5, pages 387-401, and U.S. Pat. No. 4,859,179.

To reach Class I occlusion, the prior art orthodontic brackets take an extended period of time, anchorage and springs are usually required.

The prior straight archwire technique has several drawbacks. As the bracket slot is straight, the forces to move teeth are excessive (there is no tipping movement but sliding with a large amount of friction). This means that there will be iatrogenic or undesired movements of the teeth from where forces are applied to where the physician wants them to act. To prevent this undesired movement, it becomes necessary to anchor the teeth from where forces are applied by means of additional uncomfortable devices such as transpalatal bars or extra-oral orthodontic headgear. In the present technique, these anchor devices are not necessary as teeth tip without friction to its final position. It is from this final position that the non-engaging lid changes for the engaging one to upright the teeth roots.

In the tip-edge technique developed by Peter Kesling, non-friction movement is possible because of tip-edge slot that allows for dental tipping, but in its technique additional springs are used to upright the teeth roots. In the present invention, the bracket upright force comes from the archwire which is deflected when the engaging lid is attached to the bracket in the final stage of treatment. This force is much more constant in strength throughout the treatment. In addition, different archwires sizes can be used in this final period to produce a variety of forces in comparison to a single type of spring that can be used in the tip-edge technique.

SUMMARY OF THE INVENTION

The present invention represents a qualitative technique modification of the self-uprighting bracket technique. The present invention overcome the drawbacks of the prior art by providing an orthodontic bracket assembly having a base with a rotatable body engaging the archwire and removable plate inserted into the base to retain the archwire. In addition, the removable plate can allow or prevent the rotation of the rotatable body depending on the different stages of the treatment.

An additional object of the present invention is to provide a bracket assembly in which the each of the holding members on the upper surface of the base comprises a vertical portion and a top horizontal flange or rim to define a recess for receiving the rotatable body.

A further object of the present invention is to provide a bracket assembly wherein the rotatable body comprises a circular base member; and an upper member comprised of two generally half-circular parts to form a slot between the half-circular parts for engaging the wire.

A still further object of the present invention is to provide a bracket assembly with a generally E-shaped removable plate to retain the archwire in the rotatable body and to allow or prevent the rotation of the rotatable body depending on the stages of the teeth treatment.

The present invention also provides a method of making the bracket assembly as well a method of using the bracket assembly in teeth alignment and dental treatment.

The foregoing and other objectives, features, and advantages of the invention will be more readily understood upon consideration of the following detailed description of the invention, taken in conjunction with the accompanying drawings.

DETAILED DESCRIPTION OF THE INVENTION

Although the invention will be described next in connection with certain embodiments, the invention is not limited to practice in any one specific type of orthodontic bracket assembly. The description of the embodiments of the invention is intended to cover all alternatives, modifications, and equivalent arrangements as may be included within the spirit and scope of the invention as defined by the appended claims. In particular, those skilled in the art will recognize that the components of the embodiments of the invention described herein could be arranged in multiple different ways.

Referring now to the drawings and particularly to the embodiments shown in the drawings, the orthodontic bracket assembly 11 comprises a base 20 adapted to be mounted on a tooth; a rotatable body 30 mounted on the base 20 for rotation movement with respect to the base 20 and comprising a slot 34, 35 adapted to engage a wire; and a removable plate 40 adapted to be inserted into and retained within the base 20 to secure the wire in the slot 34, 35.

The base 20 comprises a bottom surface 202, an upper surface 201 generally parallel to the bottom surface 202 and surrounding peripheral walls 203, 204, 205, 206 connecting the upper surface 201 and the bottom surface 202. Preferably, the bottom and upper surfaces 201, 202 are each in generally square or rectangular shape. There are four surrounding walls 203, 204, 205 (not shown), 206 (not shown) and opposing walls (203 and 205, 204 and 206) are parallel to each other. The bottom surface 202 of the base 20 is adapted to be mounted on or attached to a tooth surface. The possible means of mounting or attachment include adhesion by adhesives or other methods.

Preferably, four hooks 12, 13, 14, 15 in the shape of a nail or bolt are attached to or mounted on the four corners of the upper surface 201 of the base 20. The hooks can be used to hold elastic bands. An intermediate layer 25 that is generally rectangular or square shape may optionally be mounted on the upper surface 201. Alternatively, an embodiment of the present invention may not include the intermediate layer 25. The intermediate layer 25 are located at the central area of the upper surface 201 and no larger than the area defined by the four hooks 12, 13, 14, 15.

Preferably, four holding members 16, 17, 18, 19 for holding a rotatable body 30 are located near the corners of the intermediate layer 25. Alternatively, the four holding members 16, 17, 18, 19 may directly mounted on or attached to the upper surface 201 of the base 20 without the intermediate layer 25. The four holding members 16, 17, 18, 19 are positioned to form a generally square or rectangular shape with each holding member at each corner of the generally square or rectangular shape, respectively. The four holding members 16, 17, 18, 19 may be integral with the upper surface 201 or the intermediate layer 25, or alternatively, can be separate elements bonded to the upper surface 201 or the intermediate layer 25.

Figure 1:
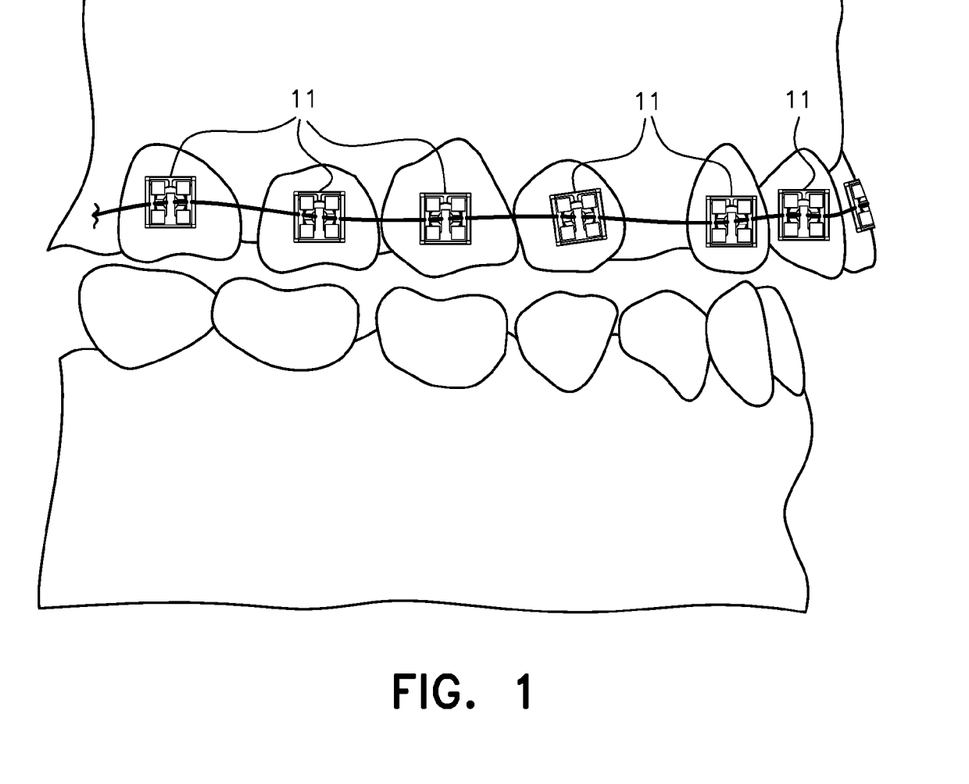
FIG. 1 is a perspective view of the embodiments of the orthodontic bracket assembly in use on teeth of a patient according to the present invention.
Figure 2:
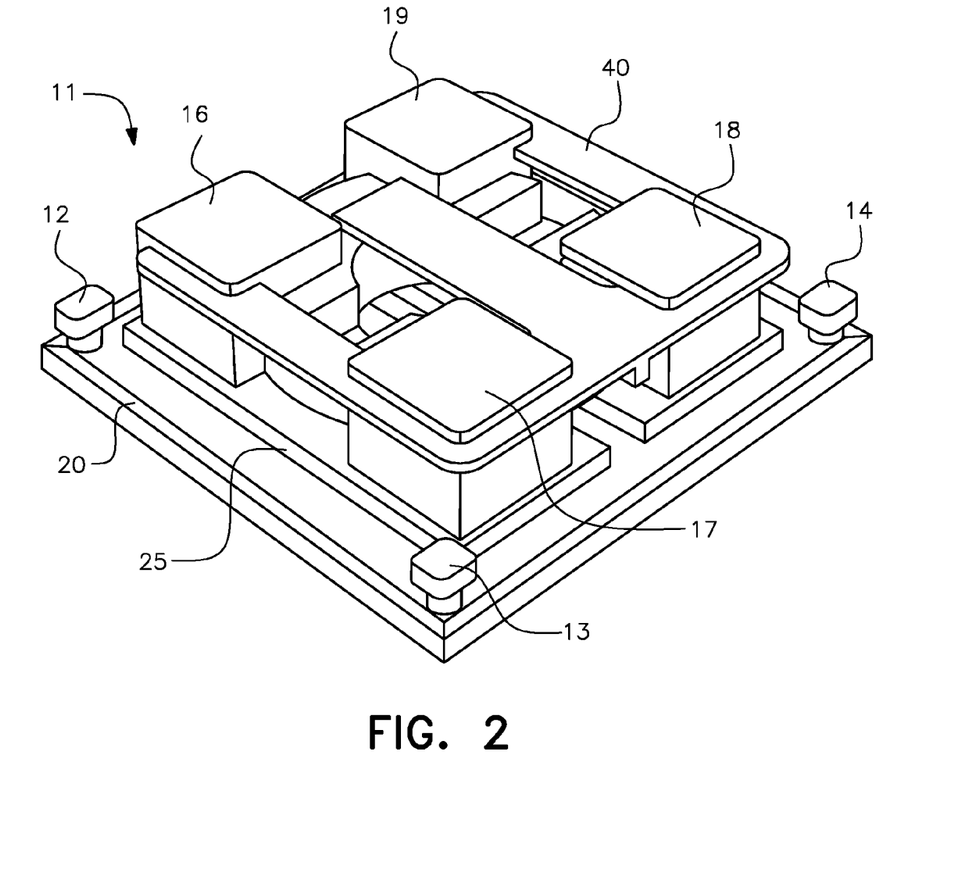
FIG. 2 is a perspective view of one embodiment of the orthodontic bracket assembly according to the present invention, where the removable plate is inserted.
Figure 3:
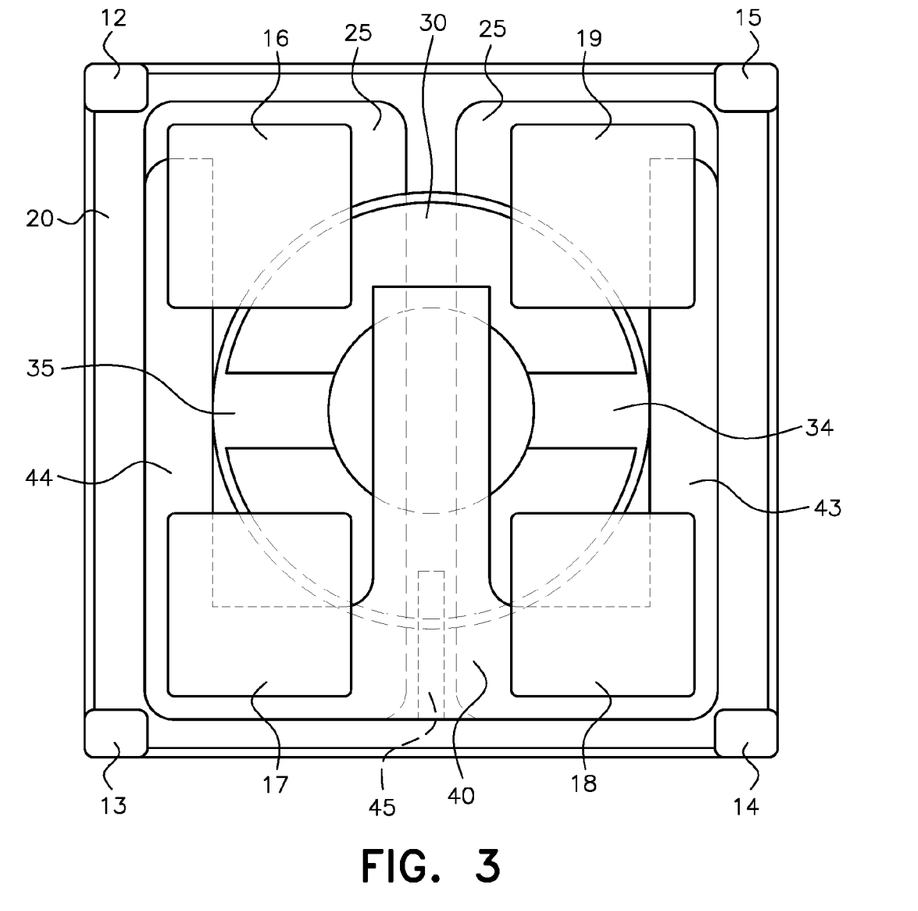
FIG. 3 is a top plan view of one embodiment of the orthodontic bracket assembly according to the present invention, wherein the removable plate is inserted.
Figure 4:
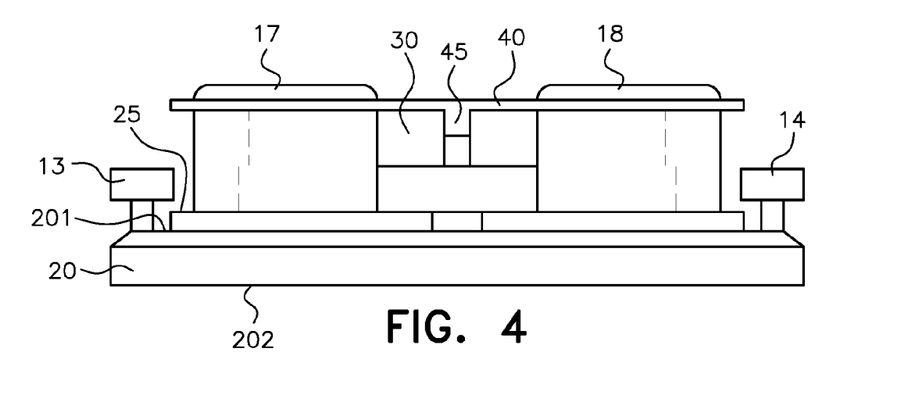
FIG. 4 is a front elevational view of one embodiment of the orthodontic bracket assembly according to the present invention, wherein the removable plate is inserted.
Figure 5:
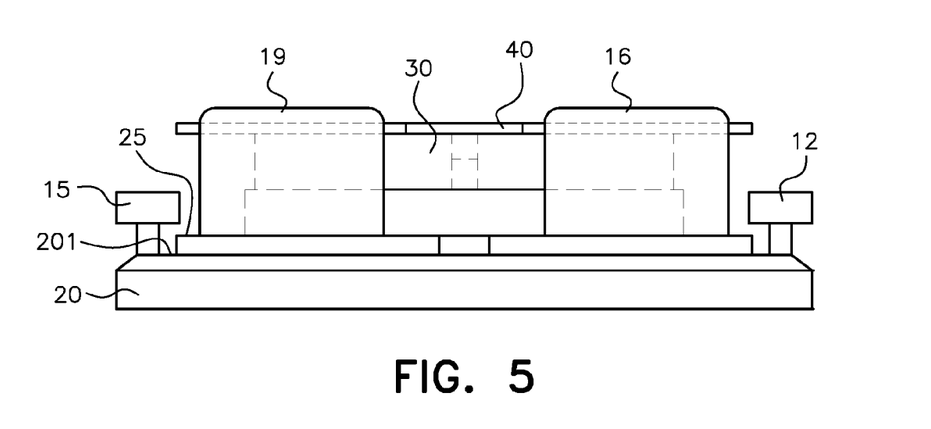
FIG. 5 is a rear elevational view of one embodiment of the orthodontic bracket assembly according to the present invention, wherein the removable plate is inserted.
Figure 6:
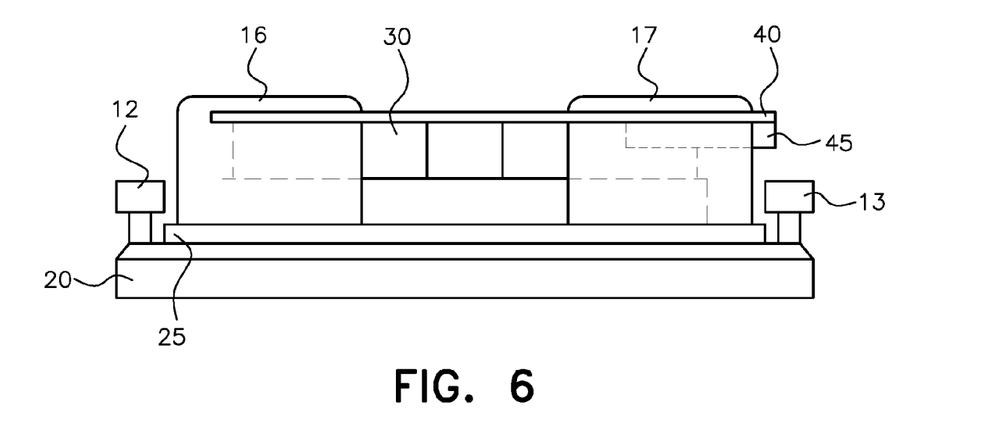
FIG. 6 is a left elevational view of one embodiment of the orthodontic bracket assembly according to the present invention, wherein the removable plate is inserted. The right elevational view is a mirror image.
Figure 7:
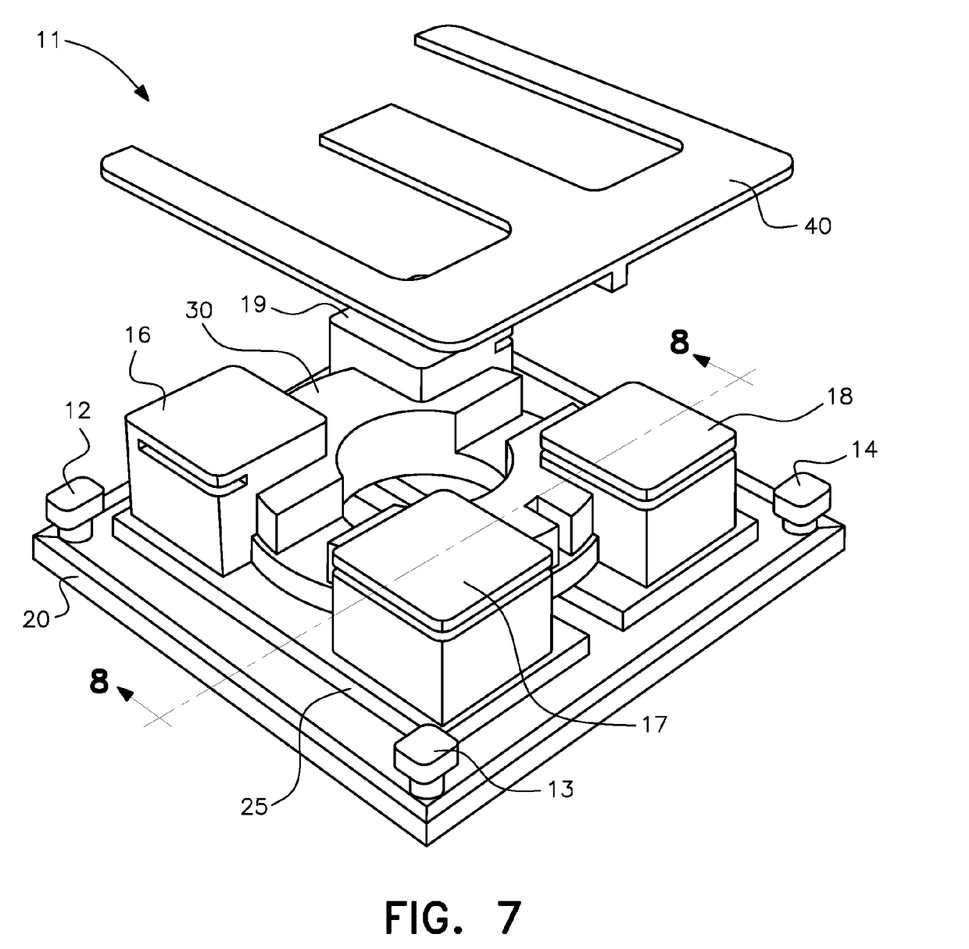
FIG. 7 is a perspective view of one embodiment of the orthodontic bracket assembly according to the present invention, wherein the removable plate is not inserted.
Figure 8:
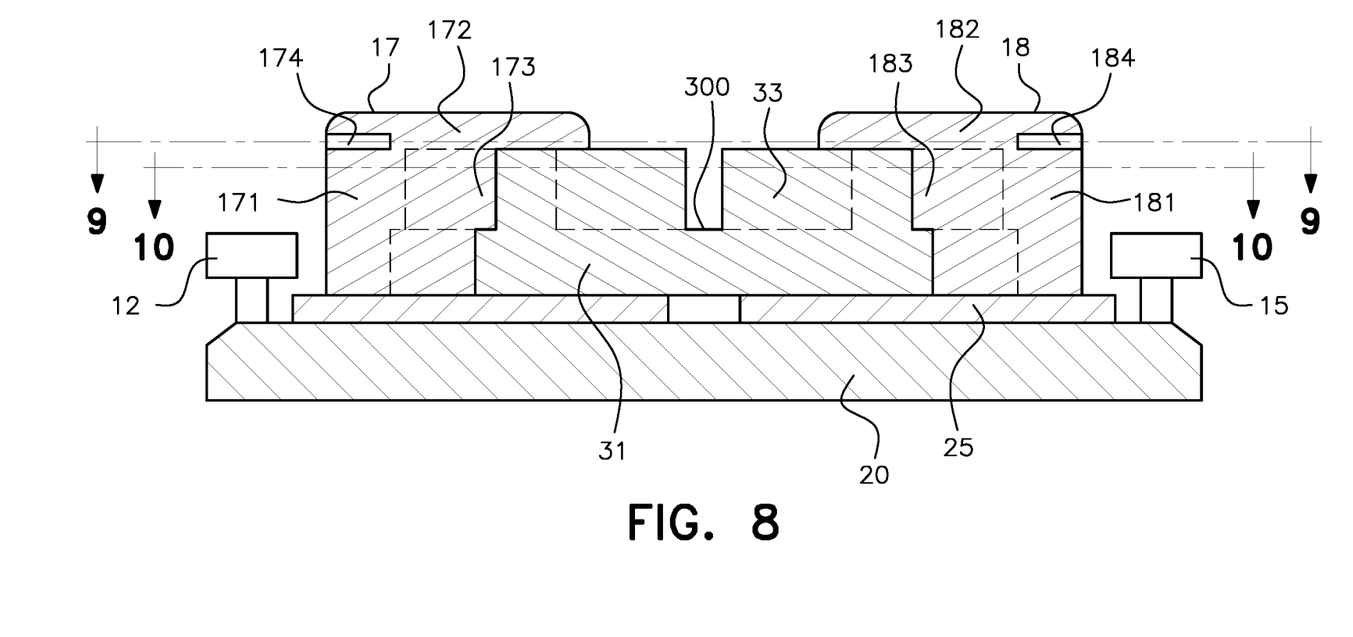
FIG. 8 is a cross-sectional view of the orthodontic bracket assembly according to the present invention along the line 8-8 in FIG. 7.
Figure 9:
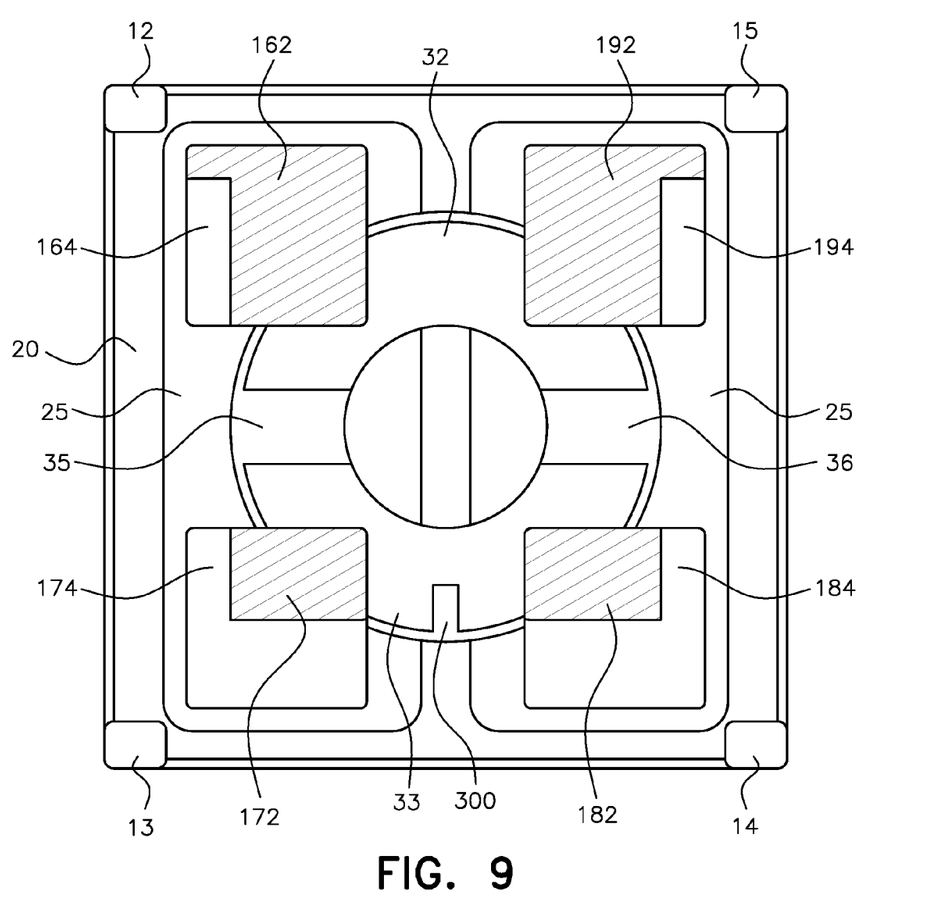
FIG. 9 is a cross-sectional view of the orthodontic bracket assembly according to the present invention along the line 9-9 in FIG. 8.
Figure 10:
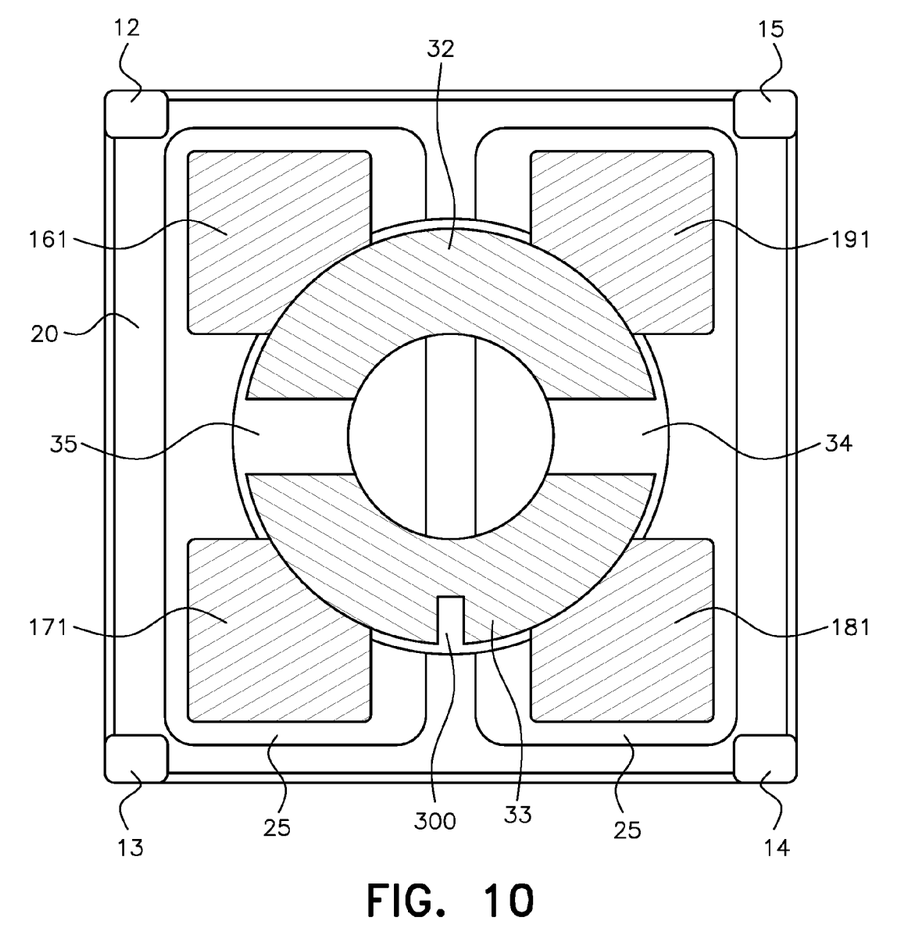
FIG. 10 is a cross-sectional view of the orthodontic bracket assembly according to the present invention along the line 10-10 in FIG. 8.
Figure 11:
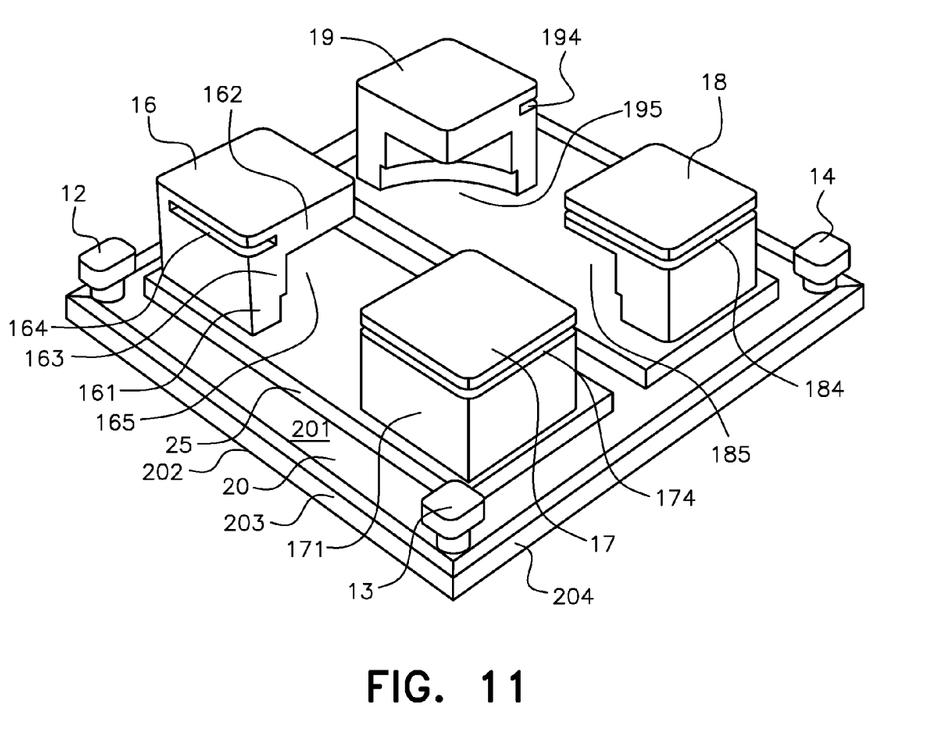
FIG. 11 is a perspective view of a base of the orthodontic bracket assembly according to the present invention, wherein the intermediate layer comprised of two separate parts spaced apart.
Figure 12:
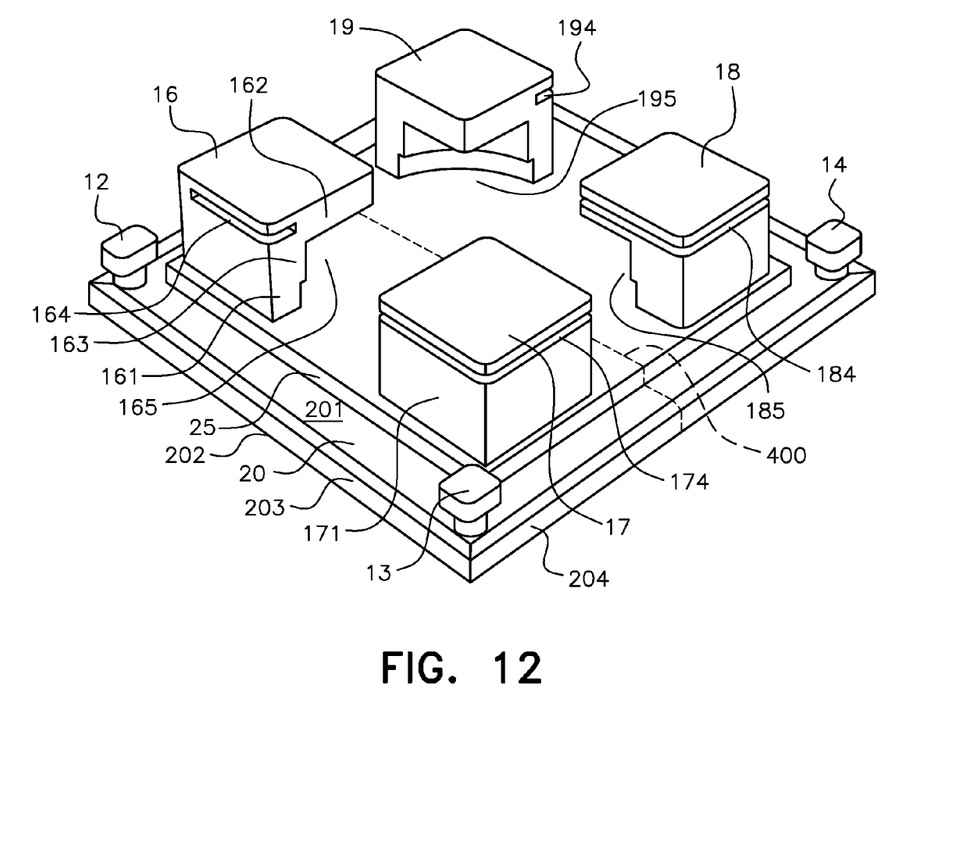
FIG. 12 is a perspective view of a base of the orthodontic bracket assembly according to the present invention, wherein two parts of the intermediate layer are welded together into an integral part.
Figure 13:
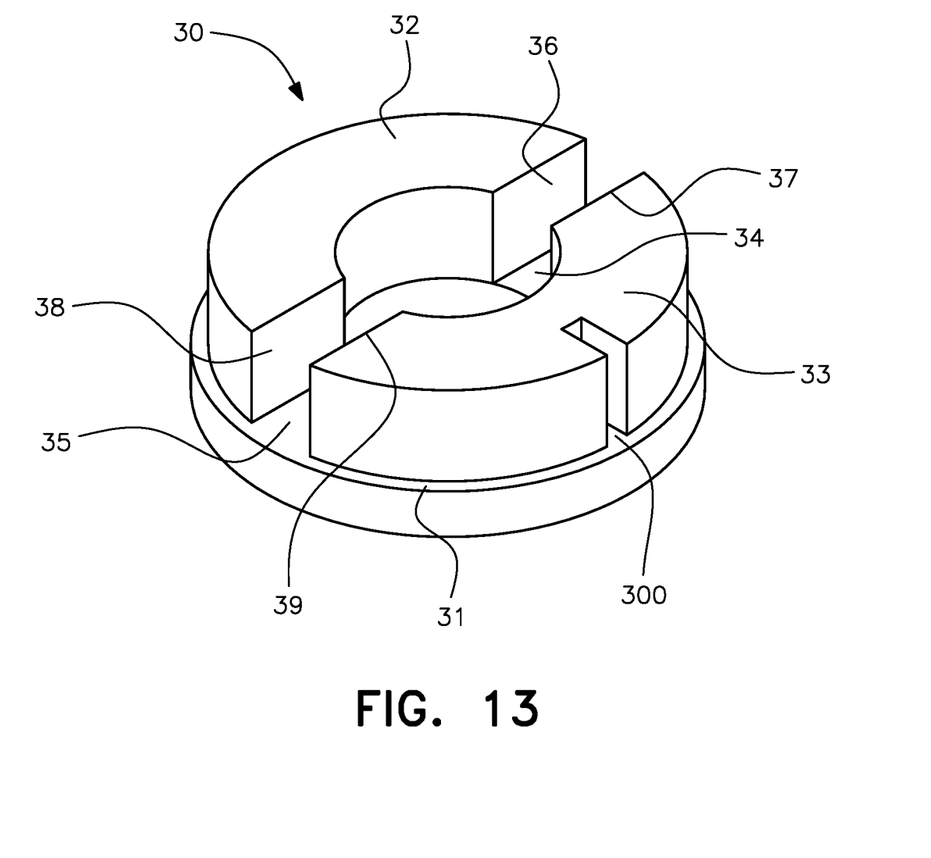
FIG. 13 is a perspective view of a rotatable body of the orthodontic bracket assembly according to the present invention.

Preferably, the four holding members 16, 17, 18, 19 extend above the upper surface 201 and the intermediate layer 25 of the base 20. Each of the holding members 16, 17, 18, 19 comprises a vertical portion 161, 171, 181, 191 and a top horizontal flange or rim 162, 172, 182, 192. For example, as shown in FIG. 11, the holding member 16 comprises a vertical portion 161 and a top horizontal flange or rim 162, The vertical portion 161 mounted on or integral with the upper surface 201 and the intermediate layer 25 of the base 20 and extends above the upper surface 201 and the intermediate layer 25 of the base 20 in a direction away from the base 20. The top horizontal flange or rim 162 is in connection with or integral with the vertical portion 161 at an end of the vertical portion 161 distal to the base 20. The top horizontal flange or rim 162 is parallel to the upper surface 201 of the base 20 and generally vertical to the vertical portion 161. The flange or rim is preferably a generally square flange or rim, in particularly, in a generally cuboid shape.

Each of the four holding members 16, 17, 18, 19 comprises a recess 165, 175, 185, 195 for holding the rotatable body 30 and a slit 164, 174, 184, 194 for receiving the removable plate 40. The recess 165, 175, 185, 195 is formed between the upper surface 201 of the base 20 or the intermediate layer 25 and the top horizontal flange or rims 162, 172, 182, 192 of the holding members 16, 17, 18, 19. The recess 165, 175, 185, 195 is preferably in the shape of steps 163 of a staircase with the lower or starting step based on the upper surface 201 or intermediate layer 25 of the base 20. This means that the vertical portion and top horizontal flange or rim of the each holding member are in upside down staircase shape complementary to the recess, such that the starting step begins at the square flange of the top horizontal flange or rim. The recess 165, 175, 185, 195 allows for inserting and retaining therein a part of the rotatable body 30 by the top horizontal flange or rim of each holding member through the square flange or rim. The four holding members 16, 17, 18, 19 together hold the rotatable body 30 in place by preventing it from moving away from the base 20 and at the same time allowing the rotatable body 30 to rotate. The rotatable body 30 is preferably in a circular shape. The recess 165, 175, 185, 195 and the holding members 16, 17, 18, 19 are complementary to the shape of the rotatable body 30.

Figure 14:
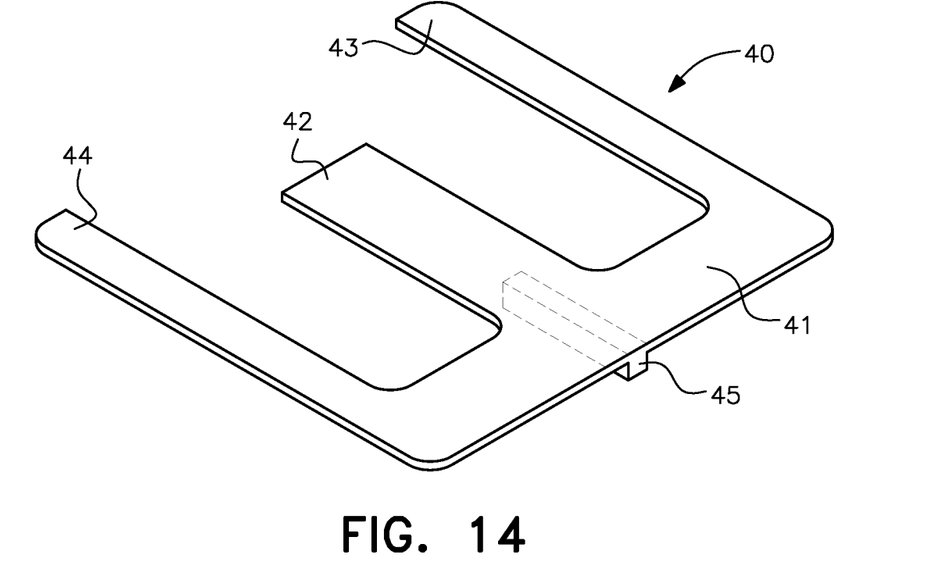
FIG. 14 is a perspective view of a removable plate (with a latch) of the orthodontic bracket assembly according to the present invention.
Figure 15:
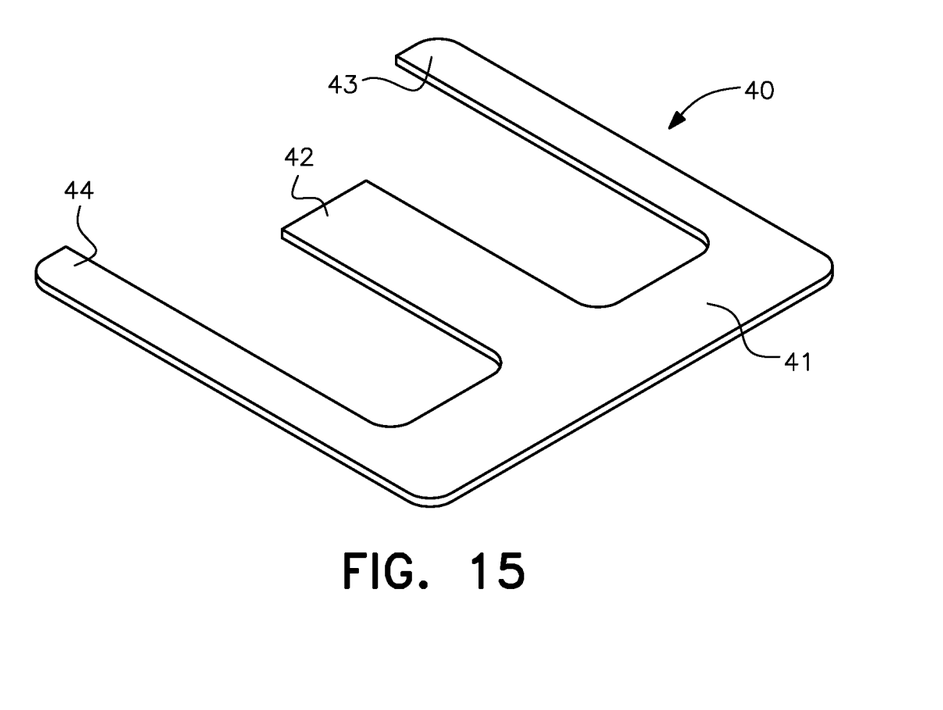
FIG. 15 is a perspective view of a removable plate (without a latch) of the orthodontic bracket assembly according to the present invention.

As stated above, each of the holding members 16, 17, 18, 19 comprises a slit 164, 174, 184, 194 for receiving and retaining a removable plate 40. The removable plate 40 is inserted into all four holding members 16, 17, 18, 19 when an archwire is inserted into the slot 34, 35 of the rotatable body 30. The shapes of the slits 164, 174, 184, 194 are complementary to parts of the removable plate 40 that is inserted into the holding members 16, 17, 18, 19. As shown in FIGS. 14-15, the removable plate 40 is in generally an E-shape and comprises a backbone part 41 in connection with a middle leg 42 and two outer legs 43, 44 on each side of the middle leg 42, all legs 42, 43, 44 being generally vertical to the backbone part 41. Two adjacent holding members 16, 19 each comprises a slit 164, 194 that is able to receive at least a part of one of the outer legs 43, 44 of the E-shaped removable plate 40. The other two adjacent holding members 17, 18 each comprises a slit 174, 184 that is able to receive at least a part of the backbone 41 and a part of the outer leg 43, 44 in connection with the backbone 41 of the E-shaped removable plate 40. The slits 164, 174, 184, 194 are generally located at the top horizontal flange or rims 162, 172, 182, 192 of the holding members 16, 17, 18, 19, in particular, the square flanges or rims of the holder members. The vertical distance between the slit 164, 174, 184, 194 and the upper surface 201 of the base 20 is larger than the vertical distance between the top of the recess 165, 175, 185, 195 (the bottom surface of the square flange or rim 162, 172, 182, 192 facing the upper surface 201 of the base 20) and the upper surface 201 of the base 20.

The bracket assembly 11 of the present invention can be made according to the following steps. The base 20, the intermediate layer 25 and the holding members 16, 17, 18, 19 are made from two symmetric pieces. For example, each piece may include half base, half intermediate layer, two holding members and two hooks. After a part of the rotatable body 30 is inserted into the recess 165, 175 of two holding members 16, 17 of one of the symmetric pieces, the other symmetric piece is attached to the first symmetric piece such that another part of the rotatable body 30 is also inserted into the recess 185, 195 of other two holding members 18, 19 of the other symmetric piece. The two symmetric pieces are then joined by, for example, welding, along the line 400.

The rotatable body 30 is adapted to engage an orthodontic wire and is preferably in a generally circular shape. The rotatable body 30 comprises a circular base member 31 and an upper member 32, 33 mounted on the top of the circular base member 31. The upper member 32, 33 preferably comprises two generally half-circular part forming an upper circle. The diameter of the upper circular 32, 33 is shorter than the diameter of the circular base member 31. The upper circle 32, 33 and the circular base member 31 are preferably concentric. The two ends 36, 38 of one of the half-circular part 32 space apart from and do not contact the two ends 37, 39 of the other of the half circular part 33, such that a slot 34, 35 is formed for receiving and retaining therein an orthodontic wire between the ends 36, 37, 38, 39 of the half-circular parts 32, 33. The half-circular part 32, 33 is preferably sectionally square or rectangular shaped.

In addition, one half-circular part 33 preferably comprises a groove 300 for receiving a latch 45 of the removable plate 40 such that the rotatable body 30 is prevented from rotating when such latch 45 is inserted into the half-circular part 33 of the rotatable body 30. Such groove 300 is preferably located in a middle position of the half-circular part 33 facing away from the center of the circle formed by the half-circular parts 32, 33.

The structure of the removable plate 40 is explained as follows (see FIGS. 14-15). The removable plate 40 is in generally an E-shape and comprises a backbone part 41 in connection with three legs 42, 43, 44 that are parallel to one another and generally vertical to the backbone part 41. The backbone part 41 is preferably an elongated rectangular strip. A first leg 43 and a second leg 44 connect with the two ends of the backbone part 41, and a middle leg 42 in connection with about the middle point of the backbone part 41. The middle leg 42 can be shorter than the first leg 43 and the second leg 44. The backbone part 41, the first leg 43, the second leg 44 and the middle leg 42 are all in the same plane.

According to an alternative embodiment of the removable plate 40 as shown in FIG. 15, a latch 45 is located about the middle point of backbone part 41 of the removable plate 40. Preferably, the latch 45 is in the shape of cuboid or cube. The latch 45 can be inserted into the groove 300 on one of the half-circular part 33 of the rotatable body 30.

The components and parts of the bracket can be made with appropriate materials. For example, all bracket components are made of stainless steel except for the removable the removable plate that can be made of nickel titanium, which is an elastic metal.

This new self-ligating bracket technique acts similar to the tip-edge bracket technique in first treatment stages. As the tip-edge technique, it is a differential tooth movement edgewise technique.

In first treatment stages, the goal is to reach a class I occlusion without overbite or overjet and with teeth alignment. Thus, in this stage, the bracket will be used with the removable plate 40 that allows free movement of the rotational part, as shown in FIG. 14. The teeth will move mesiodistally by crown tipping making the need for anchorage minimum as opposed the classic edgewise technique designed by E. Angle. Due to the rotation of the circular body of the bracket during teeth movement, there is no friction between the archwise and the bracket and therefore no need for anchorage.

In this treatment as descried above, it takes much less time to reach class I occlusion than prior art, such as non-frictional technique, i.e. the tip-edge technique, and no anchorage compared to those that are based on tooth bodily controlled movement throughout the treatment. Once class I is reached, the latch bearing removable plate as shown in FIG. 15 is coupled to the bracket. This fixes the rotatable body 30 in a predetermined position in a way that the archwire is deflected. This deflection will transmit an uprighting force to the teeth.

When put to use, the bracket assembly of the present invention is attached to dental surface, with acid etching of dental surface and photopolymerization of composite material.

An example of the teeth alignment method of the present invention may comprise the following steps:

attaching the bases of the bracket assemblies to a plurality of teeth, respectively;

inserting a wire through the slots of the rotatable bodies of the bracket assemblies, respectively;

inserting a first group of removable plates into the bases of the bracket assemblies, respectively, wherein the first group of removable plates allow for free rotation of the rotatable bodies;

determining whether class I occlusion is reached;

removing the first group of the removable plates from the bases of the bracket assemblies, respectively;

inserting the second group of removable plates into the bases of the bracket assemblies, respectively, wherein the second group of removable plates prevent the free rotation of the rotatable bodies by latches on the second group of removable plates inserted into corresponding grooves of the rotatable bodies; and determining whether desired teeth alignment is achieved.

The great advantage of the present invention over others is that it is a combined self-ligating self-uprighting technique where all forces come from the archwire and there is no need for a spring.

While the present invention has been illustrated by a description of various preferred embodiments and while these embodiments have been described in some detail, it is not the intention of the inventors to restrict or in any way limit the scope of the appended claims to such detail. Thus, additional advantages and modifications will readily appear to those skilled in the art. The various features of the invention may be used alone or in any combination depending on the needs and preferences of the user.

The invention claimed is:

1. An orthodontic bracket assembly comprising:
   a base adapted to be mounted on a tooth;
   a rotatable body mounted on the base for rotation movement with respect to the base and comprising a slot adapted to engage a wire; and
   a removable plate adapted to be inserted into and retained within the base to secure the wire in the slot;
   wherein the rotatable body comprises:
   a circular base member with a top circular surface; and
   an upper member mounted parallelly and on toe of the top circular surface of the circular base member:
   wherein the upper member comprises two generally half-circular parts forming an upper circle on a flat plane with two ends of one half-circular part respectively opposed and spaced apart from two ends of the other half circular part, such that the slot is formed between the half-circular parts for engaging the wire; and
   wherein the upper circle and the circular base member are concentric.

2. The bracket assembly according to claim 1, wherein the base comprises:
   a bottom surface for mounting on the tooth; and
   an upper surface on which a plurality of holding members are mounted, wherein each of the holding members comprises a recess for holding a part of the rotatable body and a slit for receiving a part of the removable plate.

3. The bracket assembly according to claim 2, wherein the base further comprises an intermediate layer located between the upper surface of the base and the plurality of holding members.

4. The bracket assembly according to claim 2, wherein the base further comprises a plurality of hooks on the upper surface and spaced apart from the holding members.

5. The bracket assembly according to claim 2, wherein each of the holding members comprises:
   a vertical portion mounted on, projecting away from and generally vertical to the upper surface of the base; and
   a top horizontal flange or rim in connection with an end of the vertical portion distal to the upper surface of the base and generally parallel to the upper surface of the base;
   such that the vertical portion and the top horizontal flange or rim define a recess for receiving a part of the rotatable body.

6. The bracket assembly according to claim 5, wherein the vertical portion comprises a step structure.

7. The bracket assembly according to claim 5, wherein the top horizontal flange or rim is in a generally cuboid shape.

8. The bracket assembly according to claim 5, wherein top horizontal flange or rim comprises a slit for receiving a part of the removable plate.

9. The bracket assembly according to claim 8, wherein vertical distance between the slit and the upper surface of the base is larger than vertical distance between a bottom surface of the top horizontal flange or rim facing the upper surface of the base and the upper surface of the base.

10. The bracket assembly according to claim 2, wherein four holding members are provided and the four holding members are located at each corner of a generally rectangular or square shape formed by the four holding members on the upper surface of the base.

11. The bracket assembly according to claim 1, wherein the distance of the upper circle is shorter than the diameter of the circular base member.

12. The bracket assembly according to claim 1, wherein one of the half-circular parts comprises a groove for receiving and retaining a latch of the removable plate.

13. The bracket assembly according to claim 1, wherein the removable plate is in generally an E-shape and comprises a backbone part in connection with three legs that are parallel to one another and generally vertical to the backbone part.

14. The bracket assembly according to claim 13, wherein the three legs comprises a first leg, a second leg and a middle leg and wherein the first leg and the second leg connect with the two ends of the backbone part, and a middle leg connects with the middle point of the backbone part.

15. The bracket assembly according to claim 14, wherein a latch is located about the middle point of the backbone part and is adapted to be inserted into a corresponding grove on the rotatable body.

16. A method of teeth alignment through a plurality of orthodontic bracket assemblies of claim 1, the method comprising the steps of:
   attaching the bases of the bracket assemblies to a plurality of teeth, respectively;
   inserting a wire through the slots of the rotatable bodies of the bracket assemblies, respectively;
   inserting a first group of removable plates into the bases of the bracket assemblies, respectively, wherein the first group of removable plates allow for free rotation of the rotatable bodies;
   determining whether class I occlusion is reached;
   removing the first group of the removable plates from the bases of the bracket assemblies, respectively;
   inserting the second group of removable plates into the bases of the bracket assemblies, respectively, wherein the second group of removable plates prevent the free rotation of the rotatable bodies by latches on the second group of removable plates inserted into corresponding grooves of the rotatable bodies; and
   determining whether desired teeth alignment is achieved;
   wherein the rotatable body comprises:
   a circular base member with a top circular surface; and
   an upper member mounted parallelly and on top of the top circular surface of the circular base member;
   wherein the upper member comprises two generally half-circular parts forming an upper circle on a flat plane with two ends of one half-circular part respectively oppose and spaced apart from two ends of the other half circular part, such that the slot is formed between the half-circular parts for engaging the wire; and
   wherein the upper circle and the circular base member are concentric.

17. An orthodontic bracket assembly comprising:
   a base adapted to be mounted on a tooth;

a rotatable body mounted on the base for rotation movement with respect to the base and comprising a slot adapted to engage a wire; and a removable plate adapted to be inserted into and retained within the base to secure the wire in the slot;

wherein the base comprises:

a bottom surface for mounting on the tooth; and an upper surface on which a plurality of holding members are mounted, wherein each of the holding members comprises a recess for holding a part of the rotatable body and a slit for receiving a part of the removable plate;

wherein the rotatable body comprises:

a circular base member with a top circular surface, and an upper member mounted parallel and on top of the top circular surface of the circular base member and comprising two generally half-circular parts forming an upper circle on a flat plane with two ends of one half-circular part respectively opposing and spaced apart from two ends of the other half circular part, such that the slot is formed between the half-circular parts for engaging the wire, one of the half-circular parts further comprising a groove for receiving and retaining a latch of the removable plate;

wherein the upper circle and the circular base member are concentric; and wherein the removable plate is in generally an E-shape and comprises a backbone part in connection with three legs that are parallel to one another and generally vertical to the backbone part, and wherein the latch is located about a middle point of the backbone part and the latch is adapted to be inserted into the grove on one of the half-circular parts of the rotatable body.

18. A method of making an orthodontic bracket comprising the step of:

providing a first base with a first bottom surface for mounting on a tooth and a first upper surface comprising a first and a second holding members, wherein each of the first and second holding members comprises a recess for holding a part of a rotatable body and a slit for receiving a part of a removable plate;

providing a second base with a second bottom surface for mounting on the tooth and a second upper surface comprising a third and a fourth holding members, wherein each of the third and fourth holding members comprises a recess for holding a part of the rotatable body and a slit for receiving a part of the removable plate;

inserting a circular rotatable body with a slot for engaging a wire into the recesses of the first, second, third and fourth holding members by combining the first base and the second base side by side in the same plane such that the rotatable body is rotatable with respect to the first and second bases and is prevented from being moved away from the first and second bases; and fixedly attaching the first base and the second base together;

wherein the rotatable body comprises:

a circular base member with a top circular surface; and an upper member mounted parallelly and on top of the top circular surface of the circular base member;

wherein the upper member comprises two generally half-circular parts forming an upper circle on a flat plane with two ends of one half-circular part respectively oppose and spaced apart from two ends of the other half circular part, such that the slot is formed between the half-circular parts for engaging the wire; and wherein the upper circle and the circular base member are concentric.

19. The method according to claim 18, wherein the first base and the second base are fixedly attached together by welding.

* * * * *